US00PP30526P3

(12) United States Plant Patent
Klemm et al.

(10) Patent No.: US PP30,526 P3
(45) Date of Patent: May 21, 2019

(54) ***PELARGONIUM* PLANT NAMED 'KLEPZ17400'**

(50) Latin Name: *Pelargonium zonale*
Varietal Denomination: KLEPZ17400

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,931

(22) Filed: May 23, 2018

(65) Prior Publication Data

US 2018/0343779 P1 Nov. 29, 2018

(30) Foreign Application Priority Data

May 24, 2017 (CH) ..... 17-3144

(51) Int. Cl.
*A01H 5/02* (2018.01)
*A01H 6/42* (2018.01)

(52) U.S. Cl.
USPC ..... Plt./325
CPC ..... *A01H 6/425* (2018.05)

(58) Field of Classification Search
USPC ..... Plt./263.1, 324, 325
See application file for complete search history.

*Primary Examiner* — Susan McCormick Ewoldt
*Assistant Examiner* — Karen M Redden
(74) *Attorney, Agent, or Firm* — Bethany R. Roahrig; Cochran Freund & Young LLC

(57) ABSTRACT

A new *Pelargonium* plant particularly distinguished by bright salmon-colored flowers with a lighter salmon-colored border, and a bushy, round, and upright habit, is disclosed.

1 Drawing Sheet

Genus and species: *Pelargonium zonale.*
Variety denomination: 'KLEPZ17400'.

CROSS-REFERENCE TO RELATED APPLICATIONS

This application claims priority to and the benefit of Switzerland Plant Breeders Rights application filed on May 24, 2017, Application No. 17-3144, the entire contents of which are incorporated herein by reference for all purposes.

A Community Plant Variety Rights application was filed on May 31, 2017, File No. 2017/1449.

BACKGROUND OF THE NEW PLANT

The present invention comprises a new and distinct variety of *Pelargonium*, botanically known as *Pelargonium zonale* and hereinafter referred to by the variety name 'KLEPZ17400'. 'KLEPZ17400' originated from a hand-pollination in July 2010 in Stuttgart, Germany between the female Pelargonium variety 'KLEPZ08220', also commercially known as MOONLIGHT 'Fredo' (U.S. Plant Pat. No. 21,067) and the male Pelargonium variety 'KLEPZ09251', also commercially known as MOONLIGHT 'Loki' (U.S. Plant Pat. No. 22,082).

Seeds from the hand-pollination were obtained. The seeds were sown and plants were grown for evaluation. A single plant was selected in June 2011 and subsequently named 'KLEPZ17400'. In September 2011 'KLEPZ17400' was first vegetatively propagated by vegetative cuttings. 'KLEPZ17400' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Bright salmon-colored flowers with a lighter salmon-colored border; and
2. A bushy, round, and upright habit.

DESCRIPTION OF THE PHOTOGRAPH

This new *Pelargonium* plant is illustrated by the accompanying photograph which shows an overall view of the plant. The photograph is of an approximately 8 to 9-week-old plant grown in Stuttgart, Germany under greenhouse conditions in May 2015.

The colors shown are as true as can be reasonably obtained by conventional photographic procedures.

DESCRIPTION OF THE NEW VARIETY

The following detailed descriptions set forth the distinctive characteristics of 'KLEPZ17400'. The data which define these characteristics were collected from asexual reproductions carried out in Stuttgart, Germany. Data was collected on 3-month-old plants in Stuttgart, Germany under greenhouse conditions in April 2018. Color references are to The R.H.S. Colour Chart of The Royal Horticultural Society of London (R.H.S.), 5$^{th}$ edition (2007).

Classification:

*Family.*—Geraniaceae.
*Botanical.*—*Pelargonium zonale.*
*Common.*—*Pelargonium.*
*Designation.*—'KLEPZ17400'.

Parentage:

*Female parent*.—'KLEPZ08220', also commercially known as MOONLIGHT 'Fredo' (U.S. Plant Pat. No. 21,067).

*Male parent*.—'KLEPZ09251', also commercially known as MOONLIGHT 'Loki' (U.S. Plant Pat. No. 22,082).

Plant:

*Form*.—Bushy and round.

*Habit*.—Upright.

*Height* (*from top of soil*).—16.0 cm to 18.0 cm.

*Width* (*horizontal plant diameter*).—18.0 cm to 19.0 cm.

*Natural flowering season*.—April to October.

*Propagation type*.—Cuttings.

*Time to produce a finished flowering plant*.—3 months.

*Time to initiate and develop roots*.—4 weeks.

*Root description*.—Fine, white, and dense.

Stems:

*Quantity of stems per plant*.—2 to 4.

*Color*.—RHS 166A (Greyed-orange) and RHS 143B (Green).

*Surface texture*.—Sparsely pubescent.

*Stem form*.—Round.

*Diameter*.—0.7 cm to 1.0 cm.

*Length*.—3.0 cm to 12.0 cm.

*Internode length*.—2.0 cm to 2.5 cm.

*Anthocyanin*.—Present.

Leaves:

*Arrangement*.—Alternate.

*Shape*.—Reniform.

*Apex*.—Round.

*Base*.—Closed.

*Margin*.—Crenate.

*Surface texture* (*both upper and lower surfaces*).—Sparsely pubescent.

*Length*.—3.2 cm to 5.0 cm.

*Width*.—4.5 to 7.5 cm.

*Color*.—Upper surface: RHS 147A (Yellow-green). Lower surface: RHS 147B (Yellow-green).

*Zonation*.—Present.

*Zonation color*.—RHS N189A (Greyed-green).

*Zonation conspicuousness*.—Medium.

*Zonation position*.—Middle towards margin.

*Zonation width*.—1.2 cm to 2.0 cm.

*Petiole*.—Length: 4.0 cm to 5.0 cm. Diameter: 0.2 cm to 0.4 cm. Color: RHS 144A (Yellow-green). Strength: Moderate.

*Venation pattern*.—Palmate.

*Venation color*.—Upper surface: RHS 147A (Yellow-green). Lower surface: RHS 144D (Yellow-green).

Inflorescence:

*Lastingness of flowers on the plant*.—6 to 8 days.

*Umbels*.—Quantity of umbels per plant: 3 to 5. Length: 5.0 cm to 5.5 cm. Diameter: 7.5 cm to 9.0 cm.

*Individual florets of the umbel*.—Quantity of florets per umbel: Greater than 40. Depth: 2.3 cm. Diameter: 5.2 cm.

*Fragrance*.—Absent.

Flower buds:

*Cluster shape*.—Round.

*Cluster size*.—Length: 1.2 cm to 1.5 cm. Width: 1.6 cm to 2.0 cm.

*Surface texture*.—Sparsely pubescent.

*Bud*.—Height: 0.4 cm. Width: 0.3 cm. Shape: Round. Apex: Acute. Base: Obtuse. Margin: Entire. Color: RHS 143A (Green).

Petals:

*Quantity per flower*.—7 to 9.

*Shape*.—Spatulate.

*Apex*.—Round.

*Base*.—Obtuse.

*Margin*.—Entire.

*Length*.—2.4 cm to 2.7 cm.

*Width*.—1.4 cm to 1.7 cm.

*Surface texture* (*both upper and lower surfaces*).—Smooth.

*Color of lobes*.—Upper lobes: Upper surface: RHS 69A (Red-purple) border about 1.0 cm wide, RHS 41C (Red) of about 1.4 cm from the middle to center and RHS 96A (Violet-blue) about 0.3 cm wide. Lower surface: RHS 96A (Violet-blue). Lower lobes: Upper surface: RHS 69A (Red-purple) border about 1.0 cm wide, RHS 41C (Red) of about 1.4 cm from the middle to center and RHS 96A (Violet-blue) about 0.3 cm wide. Lower surface: RHS 69A (Red-purple).

Petaloids:

*Quantity per flower*.—1 to 3.

*Shape*.—Mixed.

*Apex*.—Mixed.

*Base*.—Obtuse.

*Margin*.—Entire.

*Length*.—0.3 cm to 2.0 cm.

*Width*.—0.2 cm to 1.1 cm.

*Surface texture* (*both upper and lower surfaces*).—Smooth.

*Color*.—Upper surface: RHS 69A (Red-purple) with RHS 41C (Red) stripes. Lower surface: RHS 69A (Red-purple) with RHS 38A (Red) stripes.

Sepals:

*Number per flower*.—5.

*Shape*.—Elliptic.

*Apex*.—Acute.

*Base*.—Obtuse.

*Margin*.—Entire.

*Surface texture*.—Upper surface: Smooth. Lower surface: Moderately pubescent.

*Color*.—Upper surface: RHS 144A (Yellow-green) from the middle to the tip, RHS 165A (Greyed-orange) at the base to the middle. Lower surface: RHS 144A (Yellow-green) from the middle to the tip, RHS 166A (Greyed-orange) at the base to the middle.

*Length*.—1.0 cm.

*Width*.—0.4 cm.

Pedicel:

*Length*.—1.8 cm.

*Diameter*.—0.1 cm.

*Color*.—RHS 166B (Greyed-orange).

*Surface texture*.—Moderately pubescent.

Peduncle:

*Length*.—6.5 cm to 11.5 cm.

*Diameter*.—0.5 cm.

*Color*.—RHS 166A (Greyed-orange).

*Texture*.—Sparsely pubescent.

*Strength*.—Stiff.

*Anthocyanins*.—Present.

Reproductive organs:

*Stamens*.—Quantity per flower: 3 to 5. Anther length: 0.2 cm. Filament length: 0.6 cm. Filament color: RHS 69A (Red-purple) with RHS 45A (Red) tips. Pollen amount: Moderate. Pollen color: RHS 169A (Greyed-orange).

*Pistils*.—Number: 1. Stigma color: RHS 47B (Red). Style length: 0.3 cm. Style color: RHS 47B (Red). Ovary arrangement: Central. Ovary color: RHS 59A (Red-purple). Ovary diameter: 0.2 cm. Ovary length: 0.6 cm.

Fruit and seed set: None observed.

Disease and pest/insect resistance: None observed.

COMPARISON WITH PARENTAL LINES AND KNOWN VARIETY

'KLEPZ17400' is distinguished from its parents as described in Table 1:

TABLE 1

Comparison with Parential Lines

| Characteristics | 'KLEPZ17400' | Female parent 'KLEPZ08220' | Male Parent 'KLEPZ09251' |
|---|---|---|---|
| Leaf zonation | Medium Medium vigor, | Weak | Very strong |

TABLE 1-continued

Comparison with Parential Lines

| Characteristics | 'KLEPZ17400' | Female parent 'KLEPZ08220' | Male Parent 'KLEPZ09251' |
|---|---|---|---|
| Growth and habit | Mounding, and well-branched | Very compact | Medium, upright, dominant branches |

'KLEPZ17400' can be compared to the commercial variety 'Savannah Light Salmon' (also known as 'Duesalisal'; U.S. Plant Pat. No. 26,145). Differences between the two varieties are described in Table 2:

TABLE 2

Comparison with Similar Variety

| Characteristics | 'KLEPZ17400' | Commerical line Savannah Light Salmon |
|---|---|---|
| Leaf color | Dark-green | Green |
| Flower Color | Bright-salmon with light salmon border | Light salmon |

We claim:

1. A new and distinct variety of *Pelargonium* plant named 'KLEPZ17400' as illustrated and described herein.

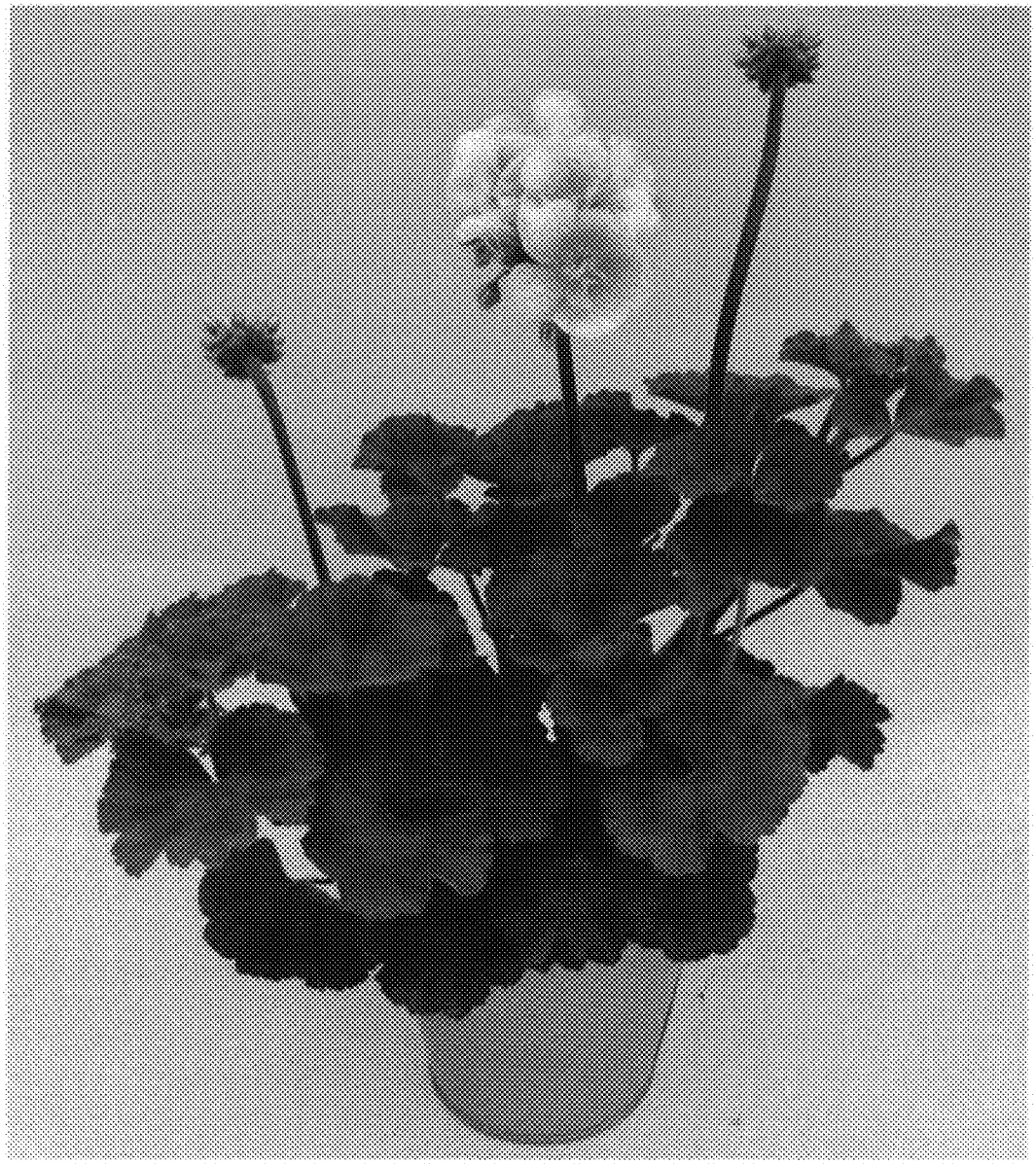

* * * * *